United States Patent [19]
McAninch

[11] Patent Number: 5,316,544
[45] Date of Patent: May 31, 1994

[54] SPLINT PAD

[75] Inventor: Thomas S. McAninch, Detroit, Mich.

[73] Assignee: Detroit Receiving Hospital & University Health Center, Detroit, Mich.

[21] Appl. No.: 71,329

[22] Filed: Jun. 2, 1993

Related U.S. Application Data

[63] Continuation of Ser. No. 836,777, Feb. 13, 1992, abandoned.

[51] Int. Cl.⁵ .......................... A61F 5/00; A61F 5/37
[52] U.S. Cl. ............................ 602/5; 602/23; 128/882
[58] Field of Search ............... 128/882, 877, 878, 879; 602/3, 5, 6, 12, 20, 21, 22, 32, 33, 34, 40, 46, 60, 62, 63, 64, 76

[56] References Cited

U.S. PATENT DOCUMENTS

| | | | |
|---|---|---|---|
| 1,242,688 | 10/1917 | Hawley | 602/33 |
| 3,238,939 | 3/1966 | Stubbs | 602/64 |
| 3,256,882 | 6/1966 | Huber | 602/60 |
| 3,535,718 | 10/1970 | Murcott | 128/882 |
| 3,762,405 | 10/1973 | DeGeorge . | |
| 3,827,431 | 8/1974 | Pecorella . | |
| 3,906,942 | 9/1975 | Lumb, Jr. et al. . | |
| 3,990,709 | 11/1976 | DeRogatin | 602/20 |
| 4,253,197 | 3/1981 | Posta | 2/75 |
| 4,265,230 | 5/1981 | Jordon . | |
| 4,481,941 | 11/1984 | Rolfes | 602/19 |
| 4,621,625 | 11/1986 | Powlan | 602/33 |
| 4,649,907 | 3/1987 | Whitehead et al. . | |
| 4,848,326 | 7/1989 | Lonardo . | |
| 4,905,715 | 3/1990 | Johnson | 128/882 |
| 4,915,097 | 4/1990 | West | 602/21 |
| 4,971,041 | 11/1990 | Millikan | 602/20 |
| 5,003,967 | 4/1991 | McConnell | 602/21 |
| 5,069,229 | 12/1991 | Kurth | 128/882 |
| 5,076,289 | 12/1991 | Darling | 128/878 |

OTHER PUBLICATIONS

Product Catalog entitled "Zimmer Traction Handbook", 6th Edition, Zimmer Corporation.

*Primary Examiner*—Michael A. Brown
*Attorney, Agent, or Firm*—Harness, Dickey & Pierce

[57] ABSTRACT

A removable pad to be placed on the thigh support or ischeal ring of a leg splint such as a Thomas splint or other similar type of splint. The pad is formed of a soft absorbent material sized to completely cover the entire thigh support ring thereby eliminating patient contact therewith, and sized to fit a variety of sizes of thigh support rings. In addition, the pad is readily removable from the ring with minimal disturbance of the traction set-up and may be disposable in order to adequately ensure sanitary conditions.

20 Claims, 2 Drawing Sheets

SPLINT PAD

This is a continuation of U.S. patent application Ser. No. 836,777, filed Feb. 13, 1992, now abandoned.

FIELD OF THE INVENTION

This invention relates generally to traction splints which keep fractured bone parts in required alignment for healing and hold a broken limb in tension sufficient to ease the pain of fracture. More particularly, the present invention relates to a pad which is removably attachable to the thigh support portion or ischeal ring of a leg splint such as a Thomas splint.

BACKGROUND OF THE INVENTION

A typical traction arrangement employing a leg splint such as a Thomas or other similar type of splint is shown in FIG. 1. These splints generally consist of an elongated U-shaped portion to which traction cords are secured, attached to a thigh support ring on which a patient's thigh rests. The splint and thigh ring are most often formed of a metallic or rigid plastic material capable of causing irritation of the patient's skin upon prolonged contact or other injury due to prolonged pressure to the surrounding thigh tissue. Since the size of the splint employed in a given traction arrangement is usually based on the length and not width of the leg, these problems are prevalent in cases involving obese or other large patients whose thigh may fit fairly tightly within the support ring.

Various pad means have thus been employed to protect a patient's thigh from such contact. One of the most common ways orthopedic personnel pad a thigh ring is by wrapping it with a soft absorbent material prior to placing it under the patient's thigh. However, upon soiling such wrapping can be difficult to remove and replace without disturbing or disassembling the traction arrangement. Since it is imperative that such disturbance be minimized, orthopedic personnel often place absorbent towels between the wrapped ring and the patient's thigh, removing and replacing the towels when soiled. This method, however, is inadequate in that any soiling of the original wrap still remains, and the wrap and towels may not sufficiently pad the ring or may bunch or unevenly pad the ring, leading to points of uneven pressure. While there have been pads manufactured especially for these rings, the pads employed to date have often been inadequate in size or design to cover and pad the entire ring, leading to some skin contact or pressure points. These pads have also been difficult to remove for laundering or replacement while in use, causing unwanted disturbance in the traction set-up.

There is, therefore, a need for a splint pad which covers and pads the entire thigh support ring to reduce patient skin contact with the device as well as points of uneven pressure. Also, it is desirable that such a pad be readily removable in order to minimize disturbance to the traction set-up, especially important in cases of skeletal traction wherein traction forces are directly applied to a pin placed through the fractured bone. Finally, a pad being totally removable from the support ring for disposal or cleaning upon soiling is critical to maintaining sanitary conditions.

SUMMARY OF THE INVENTION

The splint pad of the present invention is designed such that the entire thigh support ring is covered, including the support rings means of attachment to the remainder of the splint. This pad is formed of a soft absorbent material such as a natural or synthetic sheepskin pile for contact with the patient's skin. The pile is secured onto the ring by a backing material which wraps around the ring and which is secured by fasteners such as Velcro® strips, making it readily removable even during the application of traction.

Additional objects, advantages, and features of the present invention will become apparent from the following description and appended claims, taken in conjunction with the accompanying drawings.

DETAILED DESCRIPTION OF THE PREFERRED EMBODIMENT

Figure 1:
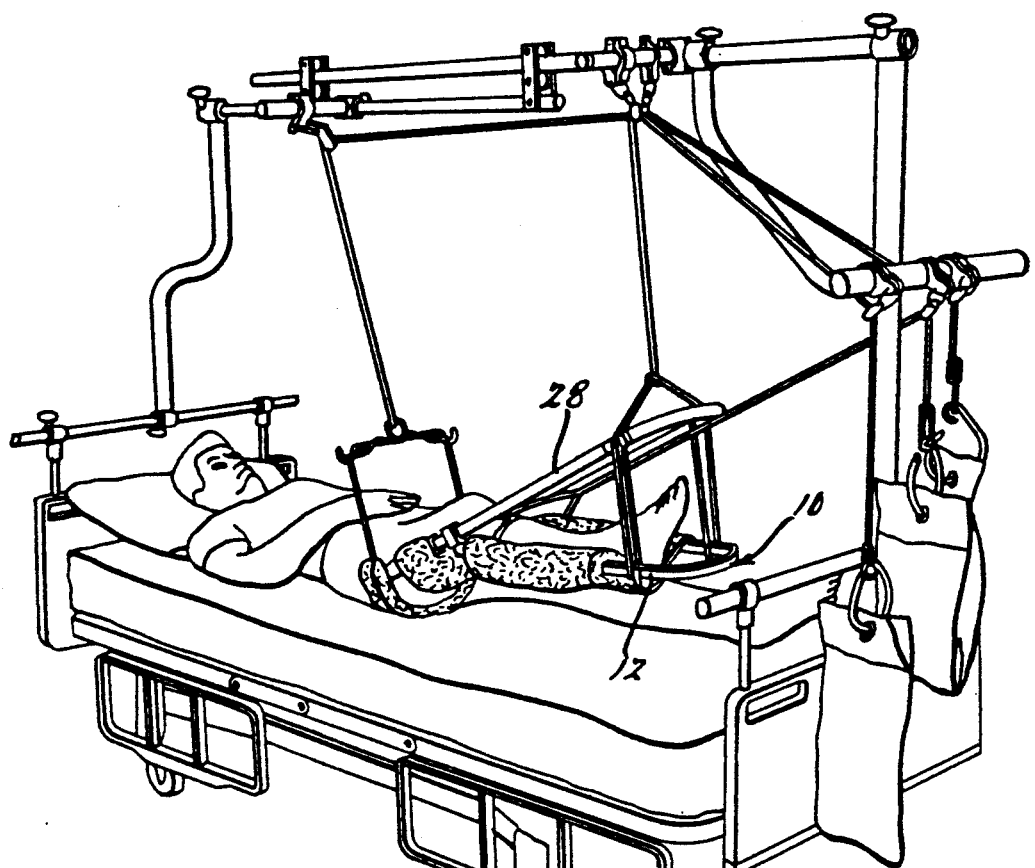
FIG. 1 is a pictorial view of a patient in traction with a leg splint such as a Thomas or other similar type of splint.
Figure 2:
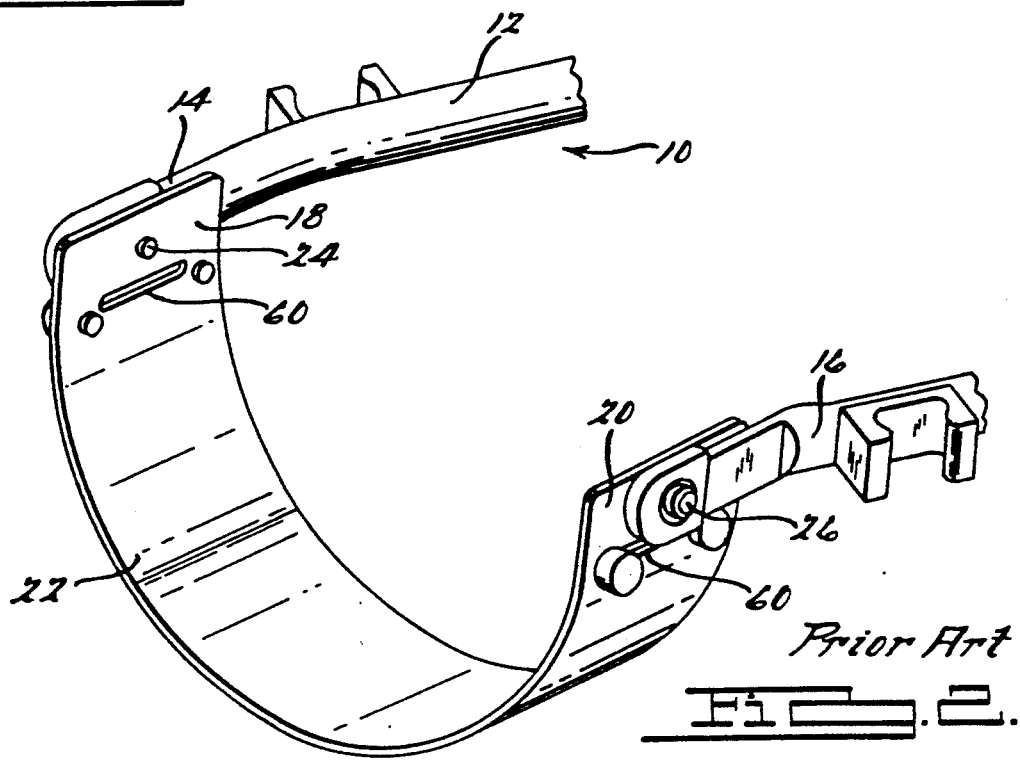
FIG. 2 is a partial perspective view of the splint showing the thigh support ring in detail.

A leg splint 10 such as a Thomas splint is shown generally in FIGS. 1 and 2 and consists of an elongated U-shaped portion 12 permanently attached at ends 14, 16 thereof to ends 18, 20 of a thigh support ring 22 by fasteners such as rivets 24, 26 or the like. The U-shaped portion 12 of splint 10 is typically formed of lightweight metal tubing which may also be radiolucent. Ring 22 is generally a rectangular piece of metal or plastic bent into a slightly skewed C-shape, the exact shape being dependent upon whether it is to be used in conjunction with traction of the right or left leg. A Pearson attachment 28 may or may not also be used in conjunction with the splint 10 in order to produce a balanced suspension system as is shown in FIG. 1.

Figure 3:
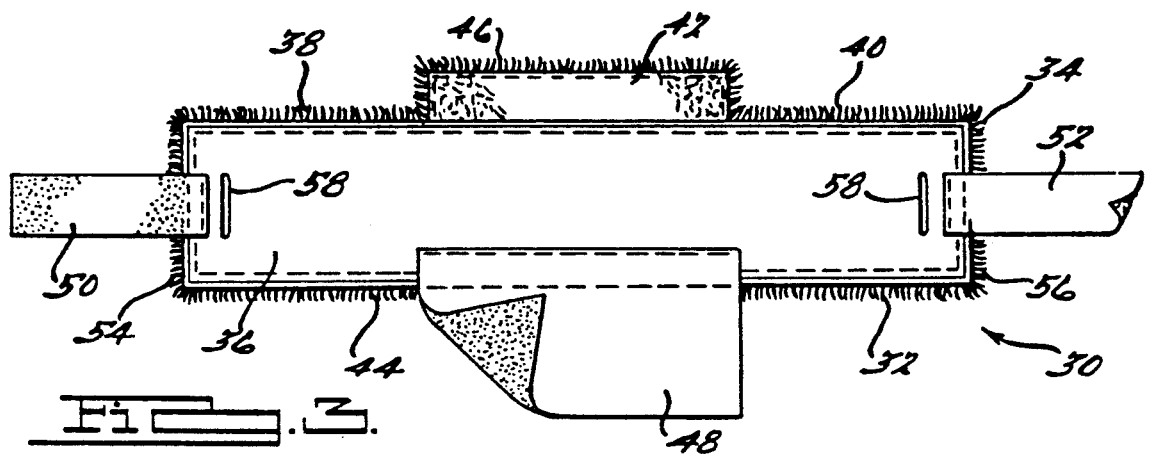
FIG. 3 is a plan view of the back side of a pad according to the teachings of the present invention.

In order to protect the patient's skin from contact with the metallic or plastic material of the thigh support ring 22, a pad 30 according to the present invention and as shown in FIG. 3 may be used. Pad 30 is preferably made from a canvas backing material 32 covered by a synthetic or natural sheepskin pile or other similar thick, cushioning material 34 which has properties so as to be soft, preferably absorbent, and non-irritating to the skin. The canvas backing 32 preferably has secured thereto on the surface opposite pile 34, a thin sheet of foam or other suitable padding material 36. Foam sheet 36 is preferably about 0.25 inch thick and generally conforming in shape to canvas 32 so as to be stitched to canvas 32 about their corresponding perimeters.

Pad 30 is generally rectangular in shape but has two rectangular cutout portions 38 and 40 along one side 42 thereof. Pad 30, intermediate said cutout portions 38 and 40, has disposed thereon along side 42 a fastener 46, preferably a Velcro® strip. Opposite fastener 46, disposed on side 44 of pad 30, is an opposing fastener 48 for joining with fastener 46 laterally around thigh support ring 22 to thereby substantially cover the ring 22. Fasteners 46 and 48 are preferably sewn to that surface of the pad 30 opposite the pile 34.

Fasteners 50 and 52, preferably strips of Velcro ® extending about 6 inches from pad 30, are mounted on sides 54 and 56 of pad 30 to secure it longitudinally around ring 22. Fasteners 46, 48 and 50, 52 could alternately be any readily removable fastening means such as snaps, tapes, and the like. Also, pad 30 may further have slots 58 formed therein to mate with corresponding slots 60 formed in thigh support ring 22 in order to allow insertion therethrough of belts or straps commonly employed in various traction arrangements.

Figure 4:
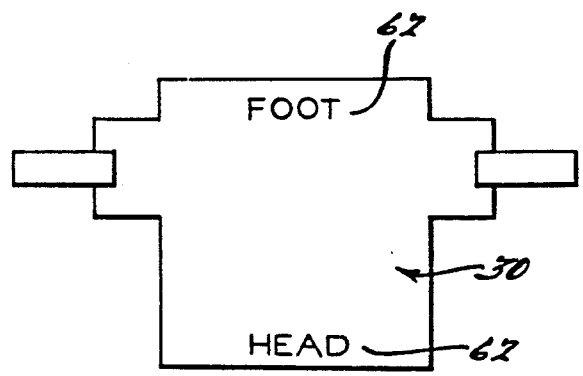
FIG. 4 is a plan view of the pad having indicator means thereon for showing orthopedic personnel correct placement on the ring.

As these splints are available in a variety of sizes, each to fit a specific size range of patients, pad 30 of the present invention is preferably of a size to fit many or all of the splint sizes, typically being about 26 inches in length by 6–8 inches in width. Also, in order to prevent incorrect placement by hospital personnel of pad 30 onto ring 22 which could lead to irreversible skin necrosis or even loss of limb due to points of uneven pressure, pad 30 preferably has an indicator 62, showing correct placement of the pad with respect to the ring, placed thereon as shown in FIG. 4. Indicator 62 preferably is permanently attached to pad 30, as by sewing, stamping or printing, and may be in the form of the words "head" and "foot" or may be arrows or any other suitable indication of correct placement of pad 30 on ring 22.

Pad 30 as described above is, therefore, designed so as to be easily attached and removed from ring 22 with minimum disturbance to the patient and traction set-up. It is also preferably made of relatively inexpensive materials so as to be disposable. This may include using synthetic Kodel ® pile rather than natural sheepskin. Disposability of this pad is preferable to laundering in order to ensure sanitary conditions. Pad 30 may also be made of fire retardant materials or be coated with a fire retardant if necessary for safety requirements.

The foregoing discussion discloses and describes merely exemplary embodiments of the present invention. One skilled in the art will readily recognize from such discussion, and from the accompanying claims, that various changes and modifications can be made therein without departing from the spirit and scope of the invention as defined in the following claims.

What is claimed is:

1. A pad removably attachable about the thigh support ring of a leg splint to protect a patient's thigh from irritating contact therewith, said pad being substantially rectangular in shape having a top, bottom and two opposing sides and comprising:
    a backing material substantially covered on one surface thereof by a cushioning material, said cushioning material being interposed between the thigh support ring of said leg splint and the patient's thigh when said pad is attached about said splint ring;
    a first pair of mating fastening means each fixedly attached to the surface of said backing material opposite said cushioning material, said first pair of fastening means extending from said top and bottom of said backing material to fasten about said ring on the side of said ring opposite the patient's thigh;
    a second pair of mating fastening means each fixedly attached to the surface of said backing material opposite said cushioning material, said second pair of fastening means extending outwardly from said opposite sides of said backing material to fasten substantially transversely over said first pair; and
    said pad being sized so as to prevent contact of the patient's thigh with said thigh support ring.

2. The pad of claim 1 wherein said backing material comprises canvas.

3. The pad of claim 1 wherein said cushioning material comprises a synthetic pile.

4. The pad of claim 1 wherein said cushioning material comprises sheepskin.

5. The pad of claim 1 wherein said first and second pairs of fastening means comprise hook and loop strips.

6. The pad of claim 1 further comprising means for indicating correct placement of said pad on said ring.

7. The pad of claim 6 wherein said means for indicating is on said backing material.

8. The pad of claim 1 wherein said thigh support ring has at least one slot formed therein to facilitate the passing of traction means therethrough and wherein said pad further comprises at least one aperture in said backing material extending through said cushioning material corresponding to said slots in said ring.

9. The pad of claim 1 further comprising a thin sheet of foam substantially covering the surface of said backing material opposite said cushioning material.

10. The pad of claim 9 wherein said foam is disposed between said backing material and said first and second fastening means.

11. The pad of claim 9 wherein said foam is attached to said backing material along their corresponding outer peripheries.

12. The pad of claim 1 wherein said leg splint is a Thomas splint.

13. A pad removably attachable to the thigh support ring of a leg splint to cushion and protect a patient's thigh from irritating contact therewith, said pad being substantially rectangular in shape having a top, bottom and two opposing sides, said top and bottom sides having a greater length than said opposing sides and comprising:
    a backing material substantially covered on one surface thereof by a layer of cushioning material, said layer of cushioning material being interposed between said thigh support ring of said leg splint and the patient's thigh when said pad is attached to the splint;
    a thin sheet of foam substantially covering the surface of said backing material opposite said cushioning material for further cushioning said patient's thigh relative to said thigh support ring;
    a first pair of mating fastening means each fixedly attached to the surface of said backing material opposite said cushioning material and extending generally transversely in opposite directions from said top and bottom sides of said backing material for fastening about said support ring on the side of said support ring opposite the patient's thigh to maintain said layer of cushioning material, in between said support ring and said patient's thigh; and
    a second pair of mating fastening means each fixedly attached to the surface of said backing material opposite said cushioning material and extending outwardly generally transversely of said first pair of mating fastening means from said opposite sides of said backing material, said second pair of fastening means fastening on the side of said support ring opposite the patient's thigh transversely over said first pair, said foam being disposed between said backing material and said first and second fastening means.

14. The pad of claim 13 wherein said leg splint is a Thomas splint.

15. The pad of claim 13 wherein said foam is attached to said backing material along their corresponding peripheries.

16. The pad of claim 13 wherein said first and second pairs of fastening means comprise hook and loop strips.

17. The pad of claim 13 wherein said cushioning material comprises natural sheepskin.

18. The pad of claim 13 wherein said cushioning material comprises synthetic pile.

19. The pad of claim 13 further comprising means for indicating correct placement of said pad on said ring.

20. A pad removably attachable to the thigh support ring of a leg splint to cushion and protect a patient's thigh from irritating contact therewith, said pad being substantially rectangular in shape having a top, bottom and two opposing sides, said top and bottom sides having a greater length than said opposing sides and comprising:

a canvas backing material substantially covered on one surface thereof by a layer of cushioning material, said layer of cushioning material comprising a natural or synthetic sheepskin pile and being interposed between said thigh support ring of said leg splint and the patient's thigh when said pad is attached to the splint;

a thin sheet of foam substantially covering the surface of said backing material opposite said cushioning material for further cushioning said patient's thigh relative to said thigh support ring, said foam being stitched to said backing material along their corresponding perimeters;

at least one slot defined in all of said backing material, said cushioning material and said foam;

a first pair of hook and loop strips each sewn to the surface of said backing material opposite said cushioning material and extending generally transversely in opposite directions from said top and bottom sides of said backing material for fastening about said support ring on the side of said support ring opposite the patient's thigh to maintain said layer of cushioning material in between said support ring and said patient's thigh;

a second pair of hook and loop strips each sewn to the surface of said backing material opposite said cushioning material and extending generally transversely of said first pair of hook and loop strips from said opposite sides of said backing material, said second pair of hook and loop strips fastening on the side of said support ring opposite the patient's thigh, transversely over said first pair of strips, said foam being disposed between said backing material and said first and second hook and loop strips; and means disposed on said pad for indicating correct placement of said pad on said ring.

* * * * *

UNITED STATES PATENT AND TRADEMARK OFFICE
CERTIFICATE OF CORRECTION

PATENT NO. : 5,316,544
DATED : May 31, 1994
INVENTOR(S) : Thomas Scott McAninch

It is certified that error appears in the above-indentified patent and that said Letters Patent is hereby corrected as shown below:

Column 4, line 54, Claim 13, after "extending" insert --outwardly and--.

Column 5, line 31, Claim 20, after "splint", insert --ring--.

Signed and Sealed this

Eighteenth Day of March, 1997

Attest:

BRUCE LEHMAN

*Attesting Officer*  *Commissioner of Patents and Trademarks*